(12) United States Patent
John

(10) Patent No.: US 7,141,047 B2
(45) Date of Patent: Nov. 28, 2006

(54) EYE ASPIRATING DEVICE AND METHOD OF USE

(76) Inventor: Thomas John, 9273 W. Falling Water Dr., Burr Ridge, IL (US) 60521

( * ) Notice: Subject to any disclaimer, the term of this patent is extended or adjusted under 35 U.S.C. 154(b) by 153 days.

(21) Appl. No.: 10/323,034

(22) Filed: Dec. 18, 2002

(65) Prior Publication Data

US 2004/0122352 A1 Jun. 24, 2004

(51) Int. Cl.
*A61M 1/00* (2006.01)
*A61M 31/00* (2006.01)

(52) U.S. Cl. .................. 604/541; 604/500; 604/902

(58) Field of Classification Search ........ 604/294–302, 604/264, 30, 313, 48, 93.01, 268, 265, 500, 604/521, 523, 540, 541, 543, 902; 606/4, 606/5, 1

See application file for complete search history.

(56) References Cited

U.S. PATENT DOCUMENTS 2,180,042 A * 11/1939 Ettinger ................... 604/35
3,929,133 A * 12/1975 Ragab ..................... 604/119
5,941,873 A * 8/1999 Korenfeld ................. 606/1

* cited by examiner

*Primary Examiner*—Cris L. Rodriguez
*Assistant Examiner*—Mark K Han
(74) *Attorney, Agent, or Firm*—John J. Connors; Connors & Assoc. Inc.

(57) ABSTRACT

An aspirating device for an eye includes a tubular member having a predetermined length that enables the tubular member to fit into an open eye and to rest on the surface of the eyeball adjacent one of the eyelids. The tubular member has one or a plurality of spaced openings therein along its length that allow liquid on the surface of the eyeball to be drawn into the tubular member upon the application of suction to the tubular member.

8 Claims, 2 Drawing Sheets

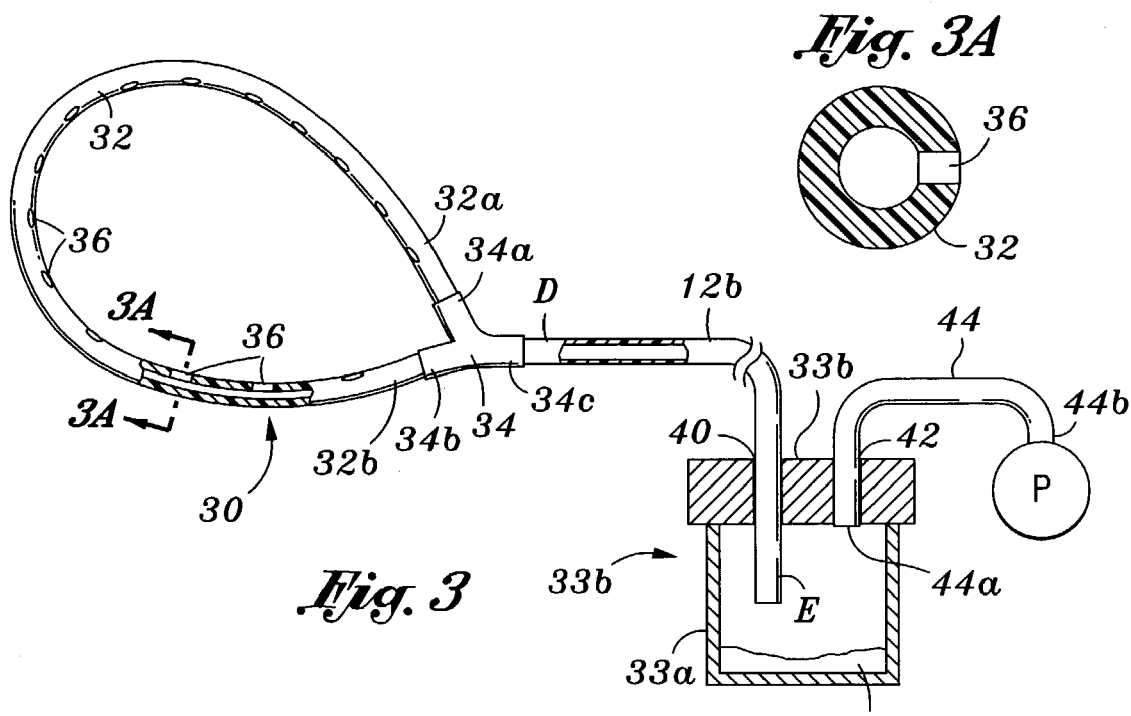
Fig. 3A
Fig. 3
LIQUID FROM EYE
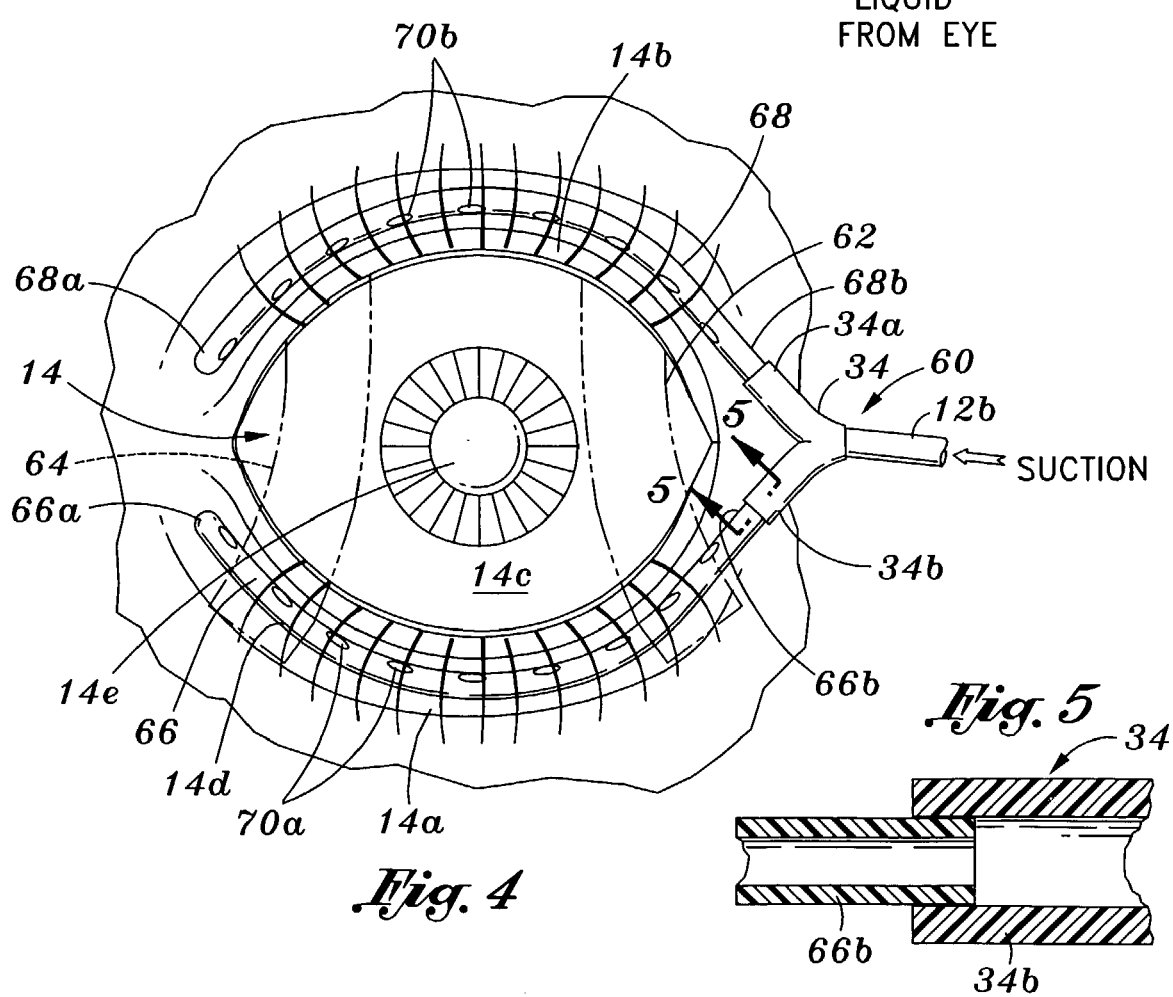
Fig. 4
SUCTION
Fig. 5

EYE ASPIRATING DEVICE AND METHOD OF USE

DEFINITIONS

The words "comprising," "having," and "including," and other forms thereof, are intended to be equivalent in meaning and be open ended in that an item or items following any one of these words is not meant to be an exhaustive listing of such item or items, or meant to be limited to only the listed item or items.

RELATED INVENTION DISCLOSURE DOCUMENT

This application is a utility patent application for an invention disclosed in Disclosure Document No. 471949, entitled "John-Aspirating Ring," received by the United States Patent & Trademark Office on Apr. 6, 2000. This Disclosure Document No. 471949 is incorporated herein by reference and made a part of this application. If any conflict arises between the disclosure of the invention in this utility application and that in the related Disclosure Document No. 471949, the disclosure in this utility application shall govern. Moreover, the inventor incorporates herein by reference any and all U.S. patents, U.S. patent applications, and other documents cited or referred to in this application or cited or referred to in the U.S. patents and U.S. patent applications incorporated herein by reference.

BACKGROUND OF INVENTION

During the course of eye surgery, blood collects on the surface of the eye. Typically, triangular cotton swabs are used to soak up this blood and other liquids used to wash the eye during the surgery. Frequently a pool of liquid forms on the eye's surface that is difficult to remove quickly using cotton swabs. This problem occurs in many types of surgery such as, for example, when implanting an intraocular lens or using lasers. It is particularly acute when the patient has very deep eye sockets. Moreover, the use of the cotton swabs frequently interferes with the view of the surgeon as he or she looks through a microscope into the open eye while conducting the surgery. Pooling of liquids on the eye causes poor visualization and makes eye surgery very difficult to perform effectively in a timely fashion. Such pooling alters the depth perception of the surgeon and this can cause potential complications or errors during surgery.

SUMMARY OF INVENTION

This invention, with its several desirable features, is summarized in the CLAIMS that follow. After reading the following section entitled "DETAILED DESCRIPTION OF SOME EMBODIMENTS OF THIS INVENTION," one will understand how the features of this invention provide its benefits, which include, but are not limited to: the provision of a low cost, easy to use, disposable eye aspirating device that eliminates pooling of liquids on the eyeball surface during surgery to provide an optimal view of the surgical field.

The aspirating device of this invention is designed to remove liquid from the surface of an eyeball of a patient with the eyelids of the patient open. Without limiting the scope of this invention as expressed by the claims that follow, some, but not all, of its features are:

One feature of the aspirating device of this invention is that it includes a tubular member having a predetermined length that enables the tubular member to fit into the open eye and to rest on the surface of the eyeball adjacent one of the eyelids. It is made of a flexible plastic tube, for example silicone plastic, having an inside diameter of from about 0.305 to about 0.325 millimeter (mm) and an outside diameter of from about 0.635 to about 0.655 mm. Consequently, the surgeon is able to manipulate and easily bend the tubular member to conform its shape to that of the curvature of the edge of the eyelid against which the member is placed. The tubular member has an overall length that is substantially equal to the width (horizontal length with patient standing) of the eye of the patient, typically from about 1 to about 1.5 inches. It comprises a flexible plastic tube, for example silicone plastic, preferably having an inside diameter of from about 0.305 mm to about 0.325 mm and an outside diameter of from about 0.635 mm to about 0.855 mm.

A second feature is that the tubular member has at least one opening, and preferably a plurality of spaced openings therein along its length. These openings allow liquid on the surface of the eyeball to be drawn into the tubular member upon the application of suction to the tubular member. Preferably, the spaced openings each have a diameter of from about 0.15 mm to about 0.18 mm and the number of openings is typically from about 2 to about 3 per centimeters (cm). These opening are usually about equally spaced apart, and they preferably face inward towards the cornea of the eye upon placement of the tubular member on the surface of the eyeball outside the surgical field avoiding interference with the surgeon's view. The opening may, however, point in other directions than towards the cornea of the eye.

In one embodiment, the tubular member is looped or oval in shape. The looped tubular member encircles a cornea of the eye and a portion of the eyeball surface surrounding the cornea. Typically, the looped tubular member has a circumference of from about 6 cm to about 7.5 cm. In one embodiment, the looped tubular member has a substantially flat side and a concave side having the openings therein. The flat side is especially adapted to rest on the surface of the eyeball. In another embodiment, the tubular member has a pair of branch tubes. The length of each tubular branch is substantially equal to the width of the eye of the patient. Preferably, each tubular branch is from about 1 to about 2 inches in length and has an inside diameter of from about 0.305 to about 0.325 mm and an outside diameter of from about 0.635 to about 0.655 mm. The spaced openings in each tubular branch preferably face inward towards the cornea of the eye upon placement of the device on the surface of the eyeball, but they point in other directions than towards the cornea of the eye. The tubular branches are connected to the extension tube to form a substantially Y configuration.

A third feature is an extension tube connected to the tubular member. This extension tube has a first end to be placed in communication with a source of suction and a second end attached to the tubular member to enable liquid drawn into the tubular member upon the application of suction to flow from the tubular member and through the extension tube. The extension tube comprises a flexible plastic tube, for example silicone plastic, having a length of from about 120 cm to about 180 cm.

A fourth feature is a holding chamber in communication with the source of suction. The source of the suction applies enough suction to suck any liquid on the eyeball surface during surgery so that the surgeon has an optimal view of the surgical field. Excessive suction is avoided, however. Typically, the suction ranges from about 30 inches of mercury (Hg) to about 45 inches of Hg. The first end of the extension tube is in communication with the holding chamber to enable the liquid that flows into the tubular member and through the extension tube to be collected in the holding chamber. The holding chamber may be a bottle at a remote location, or a plastic collection bag taped to the body of the patient.

This invention also includes a method of removing during surgery liquid from the surface of an eyeball of a patient with the eyelids of the patient open. This method includes:

(a) placing a tubular member having a plurality of spaced openings therein on the surface of the eyeball adjacent one eyelid, said tubular member having an aspiration port therein and a length that enables the tubular member to fit into the open eye, and (b) placing the aspiration port in communication with a source of suction through an extension tube connected to the aspiration port to draw the liquid into the tubular member through the openings, the liquid exiting the extension tube at a remote location.

DESCRIPTION OF DRAWINGS

Some embodiments of this invention, illustrating all its features, will now be discussed in detail. These embodiments depict the novel and non-obvious eye aspiring device and method of this invention as shown in the accompanying drawings, which are for illustrative purposes only. These drawings include the following figures (FIGS.), with like numerals indicating like parts:

FIG. 3 is a plan view of a second embodiment of the eye aspiring device of this invention connected to a holding chamber.

FIG. 3A is a cross-sectional view taken along line 3A—3A of FIG. 3.

FIG. 4 is a plan view of a third embodiment of the eye aspiring device of this invention having a pair of tubular branches showing only of branch inserted into the open eye of a patient.

FIG. 5 is a cross-sectional view taken along line 5—5 of FIG. 4.

DETAILED DESCRIPTION OF SOME EMBODIMENTS OF THIS INVENTION

Figure 1:
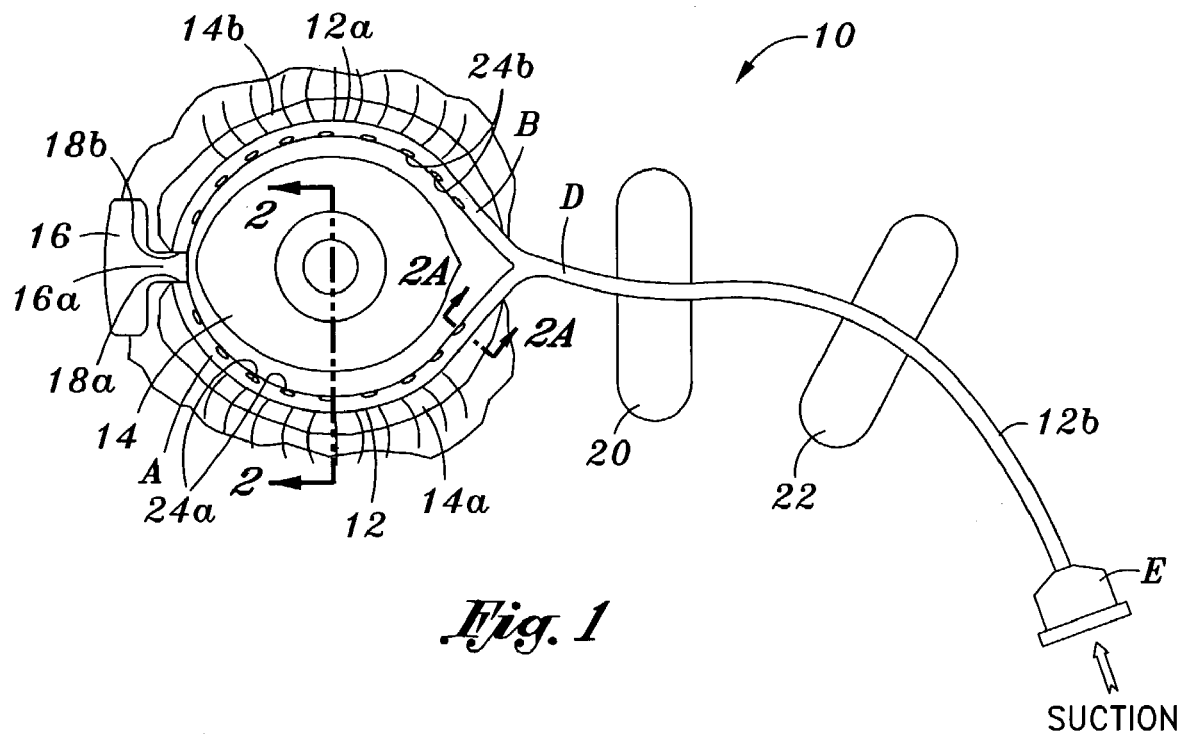
FIG. 1 is a plan view of a first embodiment of the eye aspiring device of this invention inserted into the open eye of a patient.
Figure 2:
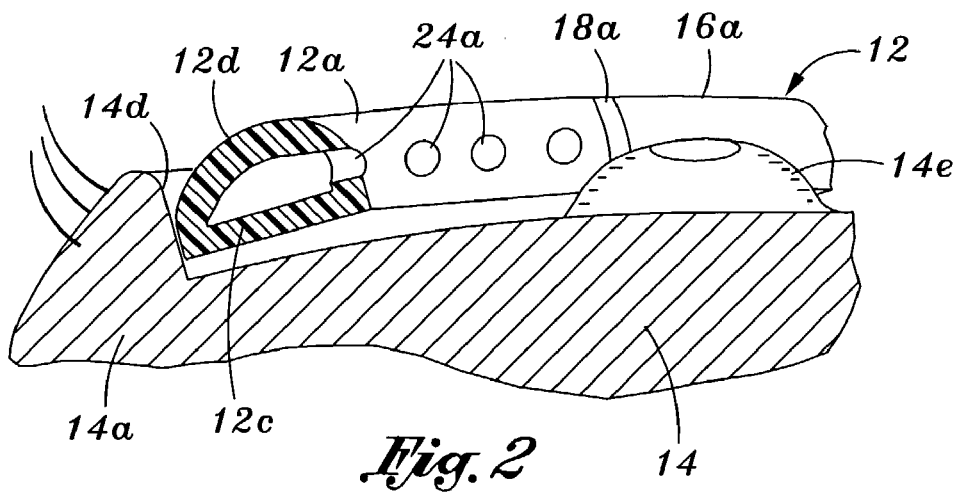
FIG. 2 is a cross-sectional view taken along line 2—2 of FIG. 1.
Figure 2A:
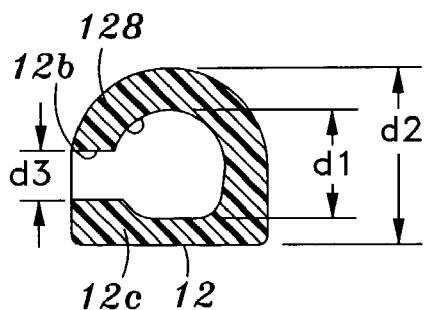
FIG. 2A is a cross-sectional view taken along line 2A—2A of FIG. 1.

As shown in FIGS. 1 and 2, the first embodiment of this invention, the eye aspirating device 10, comprises a flexible tubular member 12, preferably a transparent or translucent plastic looped tube made of a silicone material such as, for example, a siliconized elastomer. The tubular member 12 has an oval shaped section 12a that fits into an open eye 14 of a patient adjacent the eyelids 14a and 14b and a hollow extension tube 12b in communication with the oval shaped section. The posterior surface 12c of the oval shaped section 12a is substantially flat and the anterior surface 12d is substantially convex. The flat surface 12c is snug against the surface 14c of the eyeball 14 in close contact with the eye's conjunctiva. The flatness of the posterior surface 12c aids in stabilizing the device 10 during surgery. A solid T-shaped flange or tab 16 is attached to the oval shaped section 12a. This tab 16 is placed at the medial canthus of the skin surface next to the eyeball 14 to stabilize the aspirating device 10 during surgery. There are grooves 18a and 18b on each side of the leg 16a of the tab 16 that enable the surgeon to split the oval shaped section 12a into two branches. Along the extension tube 12b are additional tabs 20 and 22 also used to stabilize the device 10. Tape (not shown) may be used to attach the tabs 16, 20 and 22 to the patient's skin nearby the eyeball 14.

The size of the oval shaped section 12a is important. Its length is approximately equal that of the width of the patient's eye so that this section fits into the open eye with each side A and B snug against the formix or edge 14d of each eyelid 14a and 14b. Typically, the overall length of the oval shaped section 12a is from about 25 to about 28 mm. The circumference of the oval shaped section 12a is from about 6 cm to about 7.5 cm. The tube portion of the oval shaped section 12a has inside diameter d1 of from about 0.305 mm to about 0.325 mm and an outside diameter d2 of from about 0.635 mm to about 0.655 mm.

A series of spaced openings 24a and 24b are respectively along the inside of each side A and B of the oval shaped section 12a. There are no openings in the flat posterior surface 12c. Consequently, with the aspirating device 10 positioned in the open eye as depicted, the openings 24a and 24b face inward toward the cornea 14e of the eye 14. These openings 24a and 24b may have different shapes such as circular, square, rectangular, oval, etc. Each opening 24a and 24b has a diameter d3 of from about 0.15 mm to about 0.18 mm and the number of these openings is from about 2 to about 3 per cm. Preferably, they are substantially equally spaced apart. These opening 24a and 24b may be aligned in a row or may be offset from one another.

The openings 24a and 24b are in communication with the hollow interior 12f of the oval shaped section 12a. The extension tube 12b has one end D connected to this oval shaped section and an opposed terminal end E connected to a source of suction when the device 10 is positioned in the open eye as illustrated. Any liquid that would otherwise collect on the surface 14c of the eyeball 14 is pulled through the openings 24a and 24b into the hollow interior 12f of the oval shaped section 12a and flows through the extension tube 12b out the end E.

As depicted in FIG. 3, a second embodiment, the aspirating device 30 similar to the device 10, employs a holding chamber 33 to collect the liquid flowing from the terminal end E of the extension tube 12b. The device 30 includes a plastic tube 32 having opposed open ends 32a and 32b looped around and fitted respectively into open legs 34a and 34b of a Y connector 34. The end D of the extension tube 12b fits into the third leg 34c of the Y connector 34. There are opening 36 along the length of the tube 32 and their dimensions are substantially the same as that of the openings 24a and 24b. This tube 32 has a circular cross-section as shown in FIG. 3A, but its dimensions are substantially the same as that of the oval shaped section 12a.

The holding chamber 33 may be a bottle 33a with a cap 33b having a pair of holes 40 and 42 therein. The terminal end E of the extension tube 12b passes through the hole 40. Another tube 44 has one end 44a seated in the hole 42 and another end 44b connected to a pump P that applies suction to the bottle 33a. Preferably, the pump P has a number of different settings that allow different levels of vacuum or suction to be applied, preferably at a level of from 30 inches of Hg to 45 inches of Hg. The silicone tube 32 is bent or otherwise manipulated by twisting or bending it so that it is seated in an open eye like the device 10 and the terminal end E of the extension tube 12b is positioned inside the bottle 33a. With the aspirating device 30 so positioned, the application of suction to the bottle draws liquid on the surface 14c of the eyeball 14 through the opening 36 along the tube 32 and through the extension tube 12b to collect in the bottle 33a. The extension tube 12b has a length of from about 120 cm to about 180 cm, and approximately the same inside and outside diameters as the tube portion of the oval shaped section 12a.

As depicted in FIGS. 4 and 5, a third embodiment, the aspirating device 60 is shown positioned in an open eye. A pair of eyelid extenders 62 and 64 shown in dotted lines hold the eyelids 14a and 14b apart. The device 60 uses a pair of branch tubes 66 and 68, each having a closed distal end 66a and 68a and open proximal end 66b and 68b. The open proximal end 66b and 68b serve as aspiration ports and they are respectively inserted into the open ends 34a and 34b of the Y connector 34. The end D of the extension tube 12b is connected to the end 34c of the Y connector 34 and the other end E is connected directly or indirectly to a source of suction.

Along these branch tubes 66 and 68 are openings 70a and 70b, respectively, having essentially of the same diameter and spacing as the openings 24a and 24b. Each branch tube 66 and 68 has a length of from about 6 cm to about 7.5 cm, and these lengths are about equal. The length of the branch tubes 66 and 68 depends on the width of the patient's eye. The branch tubes 66 and 68 of aspirating devices used with children will be shorter than those used with adults.

An advantage of using the aspirating device 60 is that only one branch tube need be used. As shown in FIG. 4, the branch tube 66 is positioned adjacent the edge 14d of the eyelid 14a and against the surface 14c of the eyeball. The application of suction to the open end E of the extension tube 12b draws liquid on the surface 14c of the eyeball 14 into the openings 70a and through the hollow extension tube 12b. The other branch tube 68 is outside the eye away from the surface 14c of the eyeball 14 and not being used to remove liquid from the surface 14c of the eyeball 14.

All three embodiments of this invention are made of inexpensive materials and are disposable.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

The invention claimed is:

1. A method that substantially eliminates pooling of blood and any other liquids on a patient's eyeball surface during surgery to provide an optimal view of a surgical field, said method including the steps of, with the eyelids of the patient open,
   (a) placing a flexible tubular member having a plurality of spaced openings therein on the surface of the eyeball adjacent one eyelid, said tubular member having an aspiration port therein and a length that enables said tubular member to fit into the open eye, said length being substantially equal to the width of the eye of the patient,
   (b) positioning said tubular member on the eyeball surface snugly against an inner edge of an open eyelid with the spaced openings oriented inward away from the eyelid to enable blood and any other liquids to be drawn into the tubular member,
   (c) bending said flexible tubular member to conform said tubular member's shape to the curvature of said inner edge of the eyelid,
   (d) positioning an end of said extension tube nearby a corner of the eye with said extension tube extending outward from said corner of the eye,
   (e) placing the aspiration port in communication with a source of suction through the extension tube which is connected to the aspiration port to draw said blood and any other liquids into the tubular member through the openings, and
   (f) placing another end of the extension tube into a holding chamber at a remote location that collects said blood and any other liquids exiting the extension tube, said holding chamber being in communication with the source of suction.

2. The method of claim 1 where said source of suction is from 30 inches of Hg to 45 inches of Hg.

3. The method of claim 1 where said tubular member has an inside diameter of from 0.305 mm to 0.325 mm and an outside diameter from 0.635 mm to 0.655 mm and length of from 6 cm to 7.5 cm, and said spaced openings each have a diameter from 0.15 mm to 0.18 mm, and the number of said openings is from 2 to 3 per cm, said openings being substantially equally spaced apart.

4. The method of claim 1 where the extension tube comprises a flexible plastic tube having a length of from 120 cm to 180 cm.

5. A method that substantially eliminates pooling of blood and any other liquids on a patient's eyeball surface during implanting an intraocular lens, said method including the steps of, with the eyelids of the patient open,
   (a) placing a flexible tubular member having a plurality of spaced openings therein on the surface of the eyeball adjacent one eyelid, said tubular member having an aspiration port therein and a length that enables said tubular member to fit into the open eye, said length being substantially equal to the width of the eye of the patient,
   (b) positioning said tubular member on the eyeball surface snugly against an inner edge of an open eyelid with the spaced openings oriented inward away from the eyelid to enable blood and any other liquids to be drawn into the tubular member,
   (c) bending said flexible tubular member to conform said tubular member's shape to the curvature of said inner edge of the eyelid,
   (d) positioning an end of said extension tube nearby a corner of the eye with said extension tube extending outward from said corner of the eye,
   (e) placing the aspiration port in communication with a source of suction through the extension tube which is connected to the aspiration port to draw said blood and any other liquids into the tubular member through the openings, and
   (f) placing another end of the extension tube into a holding chamber at a remote location that collects said blood and any other liquids exiting the extension tube, said holding chamber being in communication with the source of suction.

6. The method of claim 5 where said source of suction is from 30 inches of Hg to 45 inches of Hg.

7. The method of claim 5 where said tubular member has an inside diameter of from 0.305 mm to 0.325 mm and an outside diameter from 0.635 mm to 0.65 5 mm and length of from 6 cm to 7.5 cm, and said spaced openings each have a diameter from 0.15 mm to 0.18 mm, and the number of said openings is from 2 to 3 per cm, said openings being substantially equally spaced apart.

8. The method of claim 5 where the extension tube comprises a flexible plastic tube having a length of from 120 cm to 180 cm.

* * * * *